United States Patent [19]
Fricker et al.

[11] Patent Number: 5,723,095
[45] Date of Patent: Mar. 3, 1998

[54] CLEANER CONCENTRATE FORMULATION FOR BIOLOGICAL WASTE FLUID HANDLING SYSTEMS

[75] Inventors: Christopher M. Fricker, Concord; Michelle D. Mogyordy, Willoughby, both of Ohio

[73] Assignee: Steris Corporation, Mentor, Ohio

[21] Appl. No.: 580,325

[22] Filed: Dec. 28, 1995

[51] Int. Cl.$^6$ .................................................. A61L 2/00
[52] U.S. Cl. .................. 422/292; 422/27; 422/28; 424/130; 426/316; 252/34; 252/75; 252/95; 252/174.14; 252/174.15; 252/545
[58] Field of Search ................. 422/292, 27, 28, 422/29, 50, 61; 424/130; 426/316; 252/545, 95, 75, 174.14, 174.15, 34

[56] References Cited

U.S. PATENT DOCUMENTS

| | | | |
|---|---|---|---|
| 3,969,257 | 7/1976 | Murray | 252/102 |
| 4,322,313 | 3/1982 | Raaijmakers | 252/408 |
| 4,490,389 | 12/1984 | Nelson et al. | 424/280 |
| 4,547,381 | 10/1985 | Mason et al. | 426/316 |
| 4,578,119 | 3/1986 | Marcus et al. | 134/4 |
| 4,581,374 | 4/1986 | Nelson et al. | 514/874 |
| 4,581,379 | 4/1986 | Nelson et al. | 514/690 |
| 4,601,954 | 7/1986 | Coleman | 428/522 |
| 4,602,011 | 7/1986 | West et al. | 514/187 |
| 4,686,059 | 8/1987 | Payerle | 252/75 |
| 4,743,447 | 5/1988 | LeRouzic et al. | 424/130 |
| 4,826,658 | 5/1989 | Kay | 422/30 |
| 5,091,343 | 2/1992 | Schneider et al. | 422/297 |
| 5,116,575 | 5/1992 | Badertscher et al. | 422/28 |
| 5,176,848 | 1/1993 | Kane et al. | 252/389.62 |
| 5,182,035 | 1/1993 | Schmidt et al. | 252/34 |
| 5,244,589 | 9/1993 | Liu et al. | 252/34 |
| 5,302,309 | 4/1994 | Reuben | 252/95 |
| 5,350,563 | 9/1994 | Kralovic et al. | 422/28 |
| 5,431,847 | 7/1995 | Winston et al. | 252/174.24 |
| 5,454,983 | 10/1995 | Michael et al. | 252/545 |
| 5,589,099 | 12/1996 | Baum | 510/514 |

FOREIGN PATENT DOCUMENTS

| | | |
|---|---|---|
| 186 052 | 7/1986 | European Pat. Off. . |
| 207 633 | 1/1987 | European Pat. Off. . |
| 119 560 | 7/1987 | European Pat. Off. . |
| 232 170 | 8/1987 | European Pat. Off. . |
| 332 310 | 9/1989 | European Pat. Off. . |
| 357 238 | 3/1990 | European Pat. Off. . |
| 2090369 | 1/1972 | France . |
| 2229426 | 12/1974 | France . |
| 2817858 | 10/1979 | Germany . |
| 3615787 | 11/1987 | Germany . |
| 52-110055 | 9/1977 | Japan . |
| 59-169302 | 11/1984 | Japan . |
| 61-217167 | 9/1986 | Japan . |
| 62-97692 | 5/1987 | Japan . |
| 78578 | 4/1978 | Luxembourg . |
| 410221 | 5/1934 | United Kingdom . |
| 1566671 | 5/1980 | United Kingdom . |
| 2078522 | 1/1982 | United Kingdom . |
| 96/26750 | 9/1996 | WIPO . |

OTHER PUBLICATIONS

"Journal für praktische Chemie", 334(4) (1992) 293–297.

*Primary Examiner*—Christopher Kim
*Attorney, Agent, or Firm*—Fay, Sharpe, Beall, Fagan, Minnich & McKee

[57] ABSTRACT

A vessel (14) receives biological fluid wastes. After the biological fluids wastes are drained (24) from the vessel, the vessel is sprayed (36) with a cleaning and decontaminating solution. The solution is formed by mixing water with powdered reagents including (a) a highly soluble hypochlorite, preferably lithium hypochlorite, (b) a chelator including citrate and gluconate salts and EDTA, (c) a buffer for buffering the pH to a range of 7.0 to 13.0, (d) a stabilizer for stabilizing the hypochlorite, (e) a corrosion inhibitor, preferably an organic corrosion inhibitor such as a triazole and an inorganic inhibitor such as a molybdate, and (f) a surfactant, preferably present in a concentration of 0.2 to 5%. After the interior of the vessel has been decontaminated and the drain has been closed, the solution continues to be introduced into the vessel, such that a charge of the solution is present in the vessel to decontaminate next received biological waste fluids.

22 Claims, 2 Drawing Sheets

CLEANER CONCENTRATE FORMULATION FOR BIOLOGICAL WASTE FLUID HANDLING SYSTEMS

BACKGROUND OF THE INVENTION

The present invention relates to the art of handling biological fluids. It finds application in conjunction with the collection, treatment, decontamination, and disposal of biological fluid wastes and in the cleaning and decontamination of the associated equipment. The invention finds particular application in conjunction with the disposal of medical fluid wastes in operating rooms, patient care rooms, emergency care units, and other medical facilities and will be described with particular reference thereto. However, it is to be appreciated that the present invention will also find application in conjunction with infectious fluids from other sources including mortuary, laboratory, veterinary, whole blood processing, meat processing, and other equipment which handles blood, infectious fluids, and other biological fluids.

Heretofore, various techniques have been used for collecting waste body fluids in conjunction with medical procedures. The collection vessels varied from a simple plastic bag to automated, electrically controlled processing equipment.

The receiving receptacle often varied with the nature and volume of the fluids to be collected. Typical fluids have included blood, urine, mucous, and other body discharges. During some surgical procedures, such as joint surgery, a saline solution or other rinse and lubricating fluid was selectively introduced into the surgical site. The fluid was suctioned off from time to time, removing with it surgical scraps, any blood, and other body fluids that may have entered into the surgical site.

Electronically controlled fluid waste disposal systems have been utilized, particularly when fluid waste was removed under suction. Many of these systems required direct manual interaction by medical personnel in the emptying of wastes from the collection vessel and in the rinsing or washing of the collection vessel. This created safety problems for such medical personnel, particularly when the collected wastes were infectious. Moreover, such infectious liquid wastes were often drained into the sanitary plumbing system untreated, creating potentially infectious situations in the downstream plumbing.

The present invention contemplates a new and improved biological fluid collection, handling, disinfection, and disposal system and a new and improved cleaning and decontamination formulation therefor which overcomes the above-referenced disadvantages and others.

SUMMARY OF THE INVENTION

In accordance with one aspect of the present invention, a dry decontaminant composition is provided. The composition is activated with water to form a solution for cleaning and decontaminating blood and other biological residue from surfaces. The composition comprises a hypochlorite, a chelator, a pH buffer, a stabilizer, a corrosion inhibitor, and a surfactant.

In accordance with two more limited aspects of the present invention, the hypochlorite is lithium hypochlorite and the chelator includes a citrate salt.

In accordance with another more limited aspect of the present invention, the hypochlorite is selected from a class including lithium hypochlorite, calcium hypochlorite, and mixtures thereof. The chelator is selected from a class including sodium citrate, sodium gluconate, and ethylenediaminetetraacetic acid, and mixtures thereof. The buffer is selected from a class including monosodium phosphate, disodium phosphate, sodium chloride, sodium sulfate, lithium hydroxide, sodium citrate, and mixtures thereof. The stabilizer is selected from a class including potassium sulfate, lithium chloride, lithium chlorate, and mixtures thereof.

In accordance with another aspect of the present invention, a combination of a biological waste fluid handling system and a powdered cleaning and decontaminant composition are provided. An ampule contains a premeasured dose of the composition which includes a hypochlorite, a citrate salt, a pH buffer, a stabilizer, and a surfactant. The fluid handling system includes a chamber for receiving the premeasured dose of the composition. A supply of water is connected with the mixing chamber for dissolving the composition to form a cleaning and decontaminant solution. A waste fluid collection vessel has an inlet interconnected with a flexible tube through which biological waste fluids are received. A vent is interconnected with the waste fluid vessel for connecting the interior of the vessel with at least one of atmosphere and a vacuum source. At least one vent valve selectively closes the vent such that the vessel becomes sealed, inhibiting further biological waste fluids from being received. A level sensor senses a level of biological waste fluids in the vessel. A spray nozzle is mounted to the waste fluid vessel and connected with the mixing chamber. The cleaning and decontaminant solution is selectively supplied to the spray nozzle for spraying an interior of the vessel with the cleaning and decontamination solution. A drain selectively drains waste fluid and the cleaning and decontaminant solution from the interior of the vessel.

In accordance with another more limited aspect of the present invention, a method of cleaning and microbial decontamination is provided. A hypochlorite, a chelator including a citrate salt, a pH buffer, a stabilizer, and a surfactant are mixed with water to form a solution. Biological waste fluids are collected in a vessel. The vessel is drained. After draining the vessel, an interior of the vessel is sprayed with the solution to clean and decontaminate the interior.

One advantage of the present invention resides in its improved cleaning and decontamination of biological fluid waste handling systems.

Another advantage of the present invention resides in its effective cutting of blood residue.

Another advantage of the present invention resides in its high solubility in a wide range of hard waters and water temperatures.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
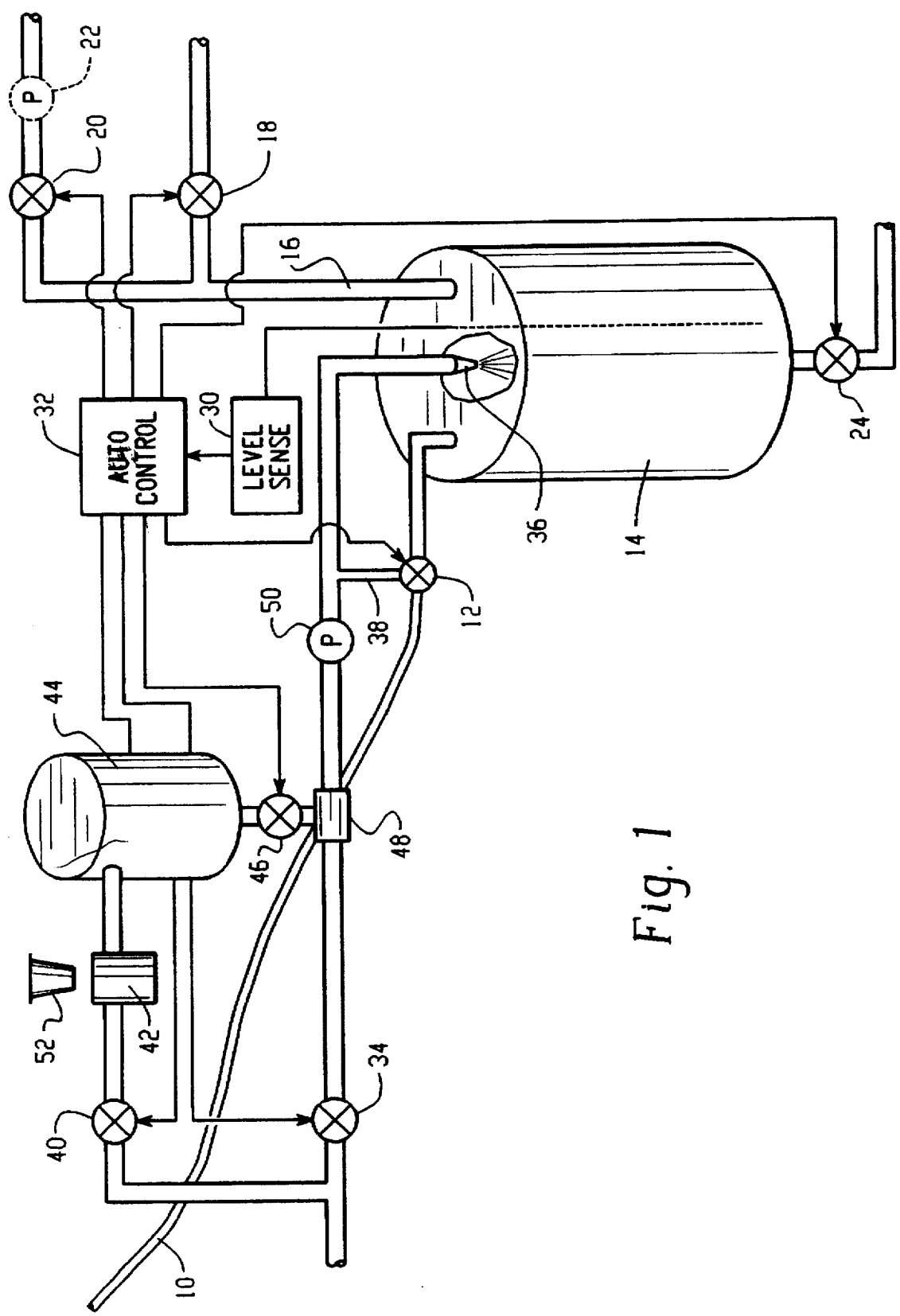
FIG. 1 is a diagrammatic illustration of an exemplary biological fluid waste handling system in accordance with the present invention.

With reference to FIG. 1, a length 10 of flexible tubing is connected with a patient or other source of biological fluid waste at one end and with an inlet valve 12 at another end. The inlet valve 12 is connected with a waste fluid receiving vessel 14 which receives the waste fluids. A vent line 16 is connected either with atmosphere by opening an atmosphere vent valve 18 or with a source vacuum by opening a vacuum vent valve 20. In most hospitals, there is a centralized vacuum source with which the vacuum vent valve 20 is connected. Optionally, a vacuum pump 22 may be connected for drawing a negative pressure on the interior of the waste fluid receiving vessel 14. A drain valve 24 is positioned at a low point of the vessel for selectively draining the vessel. In portable units, the system is wheeled to an operating room or other location of use. After the medical procedure is complete, the system is wheeled to a disposal site for draining and cleaning. Alternately, the system can be built in or stationarily positioned with the drain valve connected with the sanitary sewer.

A level sensor 30 senses the level of waste fluids in the waste fluid receiving vessel 14. When a preselected near full level is achieved, the level sensor 30 signals an automatic control circuit 32 which causes the atmospheric vent valve 16 and the suction vent valve 18 to be closed. When the vent valves are closed, additional received fluid quickly causes a slight positive pressure in the waste fluid receiving vessel 14, stopping the inflow of biological waste fluid. The automatic control circuit 32 also signals a warning to advise the operator that the vessel 14 is filled. The inlet valve 12 closes to stop more fluid from being received or changes state to divert the received fluid to another vessel (not shown).

In the portable embodiment, an operator signals the automatic control circuit to start a cleaning cycle. In the built-in embodiment, the cleaning cycle can be initiated manually by an operator or automatically in response to the vessel filling. At the start of the cleaning cycle, the automatic control 32 then causes an outlet valve 24 to open, concurrently with the atmospheric vent valve 16. When the vessel 14 is drained, the automatic control causes a water inlet valve 34 to open, allowing rinse water to flow through a spray nozzle 36 into the vessel 14. A line 38 directs the incoming water to the waste fluid inlet valve 12 to flush it and the plumbing between it and the reservoir 14.

At a preselected time, preferably when the system is first engaged, the automatic control circuit 32 opens another fluid inlet valve 40 which allows a metered amount of water to flow through a mixing chamber 42 into a reservoir 44 for holding a metered amount of a cleaner concentrate. More specifically, the operator causes a unit dose of a powdered cleaner reagents to be placed in the mixing chamber 42. The received water dissolves the powdered reagents, and where appropriate causes them to react, to form the cleaning concentrate solution.

After an initial plain water flush, the automatic control opens a cleaning solution outlet valve 46 from the cleaning concentrate reservoir 44. A venturi, metering valve, or the like 48 mixes a controlled concentration of the cleaner concentrate solution with the incoming water. The nozzle 36 sprays the water with entrained cleaner on the surfaces of the biological waste fluid receiving vessel 14 to clean and decontaminate its surfaces. After a preselected disinfection time, the drain valve 24 is closed. The clean solution valve 46 remains open such that a measured volume of the cleaning solution is deposited in the bottom of the vessel 14. The water valve 34 may remain open or partially open such that the cleaning solution is deposited in its diluted form or may be closed such that the cleaner concentrate solution is deposited in its concentrated form. The cleaning solution remains in the vessel 14 until the next use to deodorize the system and to decontaminate the next received biological fluids.

Optionally, a pump 50 can be disposed in the inlet water line to assure that flushing and cleaning fluids are supplied to the nozzle 36 under a preselected, fixed pressure. As another option, a water treatment canister, such as a water softener, can be connected with the water inlet to soften the water, eliminate impurities, or otherwise treat the incoming water. As yet another option, a second waste fluid collection vessel is provided such that when the fluid vessel 14 becomes filled, additional biological waste fluids can be channeled to the other vessel. With two waste fluid collection vessels, waste fluid can be collected simultaneously from two sources or waste fluid can be collected from a single source, with one vessel receiving the fluid while the other vessel is being drained and cleaned.

The powdered formulation is preferably shipped in a package 52 which holds a unit dose. The package is opened into the mixing chamber in each cycle, preferably in a mechanical operation to prevent direct operator contact with the formulation. The powdered formulation includes an active ingredient in the form of a strong oxidant or components which react in water to form a strong oxidant, as well as a material for cutting through blood, a pH buffer, a stabilizer, a corrosion inhibitor, and a surfactant.

More specifically to the preferred embodiment, the active ingredient is a soluble hypochlorite in a powdered form. Lithium hypochlorite is preferred due to its high solubility, although calcium hypochlorite which has a lower, but still good solubility, will find limited application.

The blood cutting ingredient is preferably an ionic citrate salt, with sodium being preferred for its high solubility. The sodium citrate functions as a chelator which attaches to the iron in the hemoglobin of blood, reducing clotting and facilitating its removal. Sodium citrate further provides an advantageous pH buffering effect. Other advantageous chelating agents for removing blood include ethylenediaminetetraacetic acid (EDTA) and sodium gluconate. Preferably, there is a blend of the EDTA, sodium citrate, and sodium gluconate chelating agents with the EDTA providing about half the chelating agent by weight and the sodium citrate and sodium gluconate each providing about a quarter of the chelating agent. The chelating agents as a whole are preferably present in about a 1:1 weight relationship with the hypochlorite.

The pH buffers are present in appropriate quantities to buffer the pH between 7.0 to 13.0, with 6.8 to 8.0 being preferred. Monosodium phosphate provides a gross pH adjustment with disodium phosphate providing the fine adjustment. The lithium hypochlorite in the form that it is commonly available is intermixed with sodium chlorite, sodium sulfate, and lithium hydroxide which provide pH buffering activity. The mono and disodium phosphates are selected in a quantity, relative to the sodium citrate, sodium chloride, sodium sulfate and lithium hydroxide to bias the pH to the 6.8 to 8.0 range.

The stabilizers stabilize the part of the reaction with the hypochlorite which creates a hypochlorous acid solution. Preferred stabilizers include potassium sulfate, lithium chloride, and lithium chlorate. Preferably, the stabilizers are present in a hypochlorite to stabilizer ratio of about 4:1 by weight, with the lithium chlorate being about half of the stabilizer and the lithium chloride and the potassium sulfate each being about a quarter of the stabilizer mixture.

Organic and inorganic corrosion inhibitors are provided for reducing corrosion on the working parts of the system, the interconnecting plumbing and valves, and downstream plumbing into which the treated waste fluids are discharged. In a preferred embodiment, the corrosion inhibitors are a mixture of about ⅔ triazoles and about ⅓ molybdates. Benzotriazoles and tolytriazoles are preferred by other azoles, benzoates, and five-membered ring compounds are contemplated, particularly for yellow and white metal corrosion resistance. Optionally, zinc complexes chromates, dichromates, tungstates, vanadates, borates, and combinations thereof can also be used to inhibit corrosion, particularly in steel and iron. Preferably, the corrosion inhibitors to hypochlorite ratio is about 1:10 ratio by weight.

The preferred dry formulation is set forth in TABLE 1.

TABLE 1

| FORMULA | PERCENT BY WEIGHT | RANGE (% BY WEIGHT) |
| --- | --- | --- |
| Lithium Hypochlorite | 23.6 | 17.5–80.0 |
| Ethylenediaminetetraacetic Acid (EDTA) | 7.6 | 3.8–11.3 |
| Sodium Citrate | 10.5 | 5.0–30.0 |
| Sodium Gluconate | 10.5 | 5.0–30.0 |
| Monosodium Phosphate | 4.0 | 3.0–6.5 |
| Disodium Phosphate | 19.5 | 18.4–23.0 |
| Sodium Chloride | 4.0 | 3.5–4.5 |
| Sodium Sulfate | 7.5 | 2.5–9.0 |
| Potassium Sulfate | 2.0 | 0.25–4.2 |
| Lithium Chloride | 2.0 | 0.25–4.2 |
| Lithium Chlorate | 1.5 | 0.75–2.6 |
| Lithium Hydroxide | 2.0 | 1.25–4.8 |
| Triazoles | 2.3 | 0.5–4.1 |
| Molybdates | 1.0 | 1.0–2.5 |
| Nonylphenoxypoly Ethanol | 1.0 | 0.1–2.5 |
| Ethoxylated Polyoxypropylene | 1.0 | 0.1–2.5 |

Figure 2:
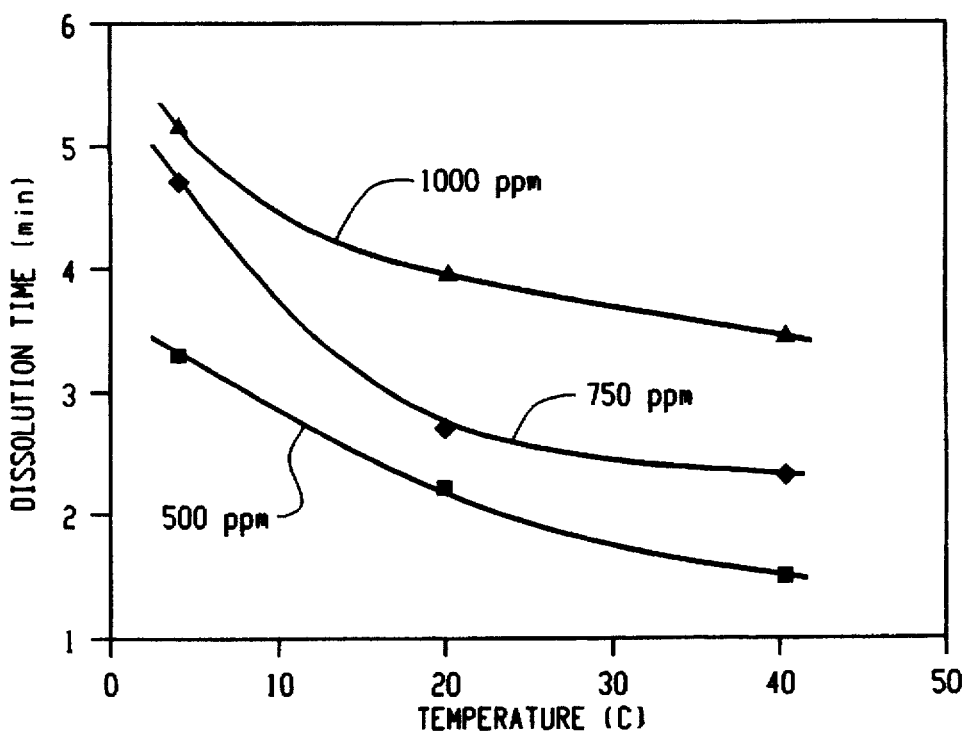
FIG. 2 is a graphical depiction of dissolution time versus temperature for 500, 750, and 1,000 ppm concentrations of the preferred cleaner concentrate formulation in hard water using continuous mechanical mixing at 500 rpm; and, FIG. 3 is a graphical depiction of percentage lithium carbonate formation versus calcium carbonate concentration in ppm of hard water with citrate concentrations of 0, 2, 5, 10, and 50%.

In the preferred embodiment, the hypochlorite is mixed with water in an appropriate ratio to achieve a 100–5000 ppm concentration of hypochlorous ions. The preferred formulation is highly soluble at a wide range of water temperatures from 4°–40° C. FIG. 2 shows minimal effect of the formulation solubility at a variety of mixing temperatures.

Figure 3:
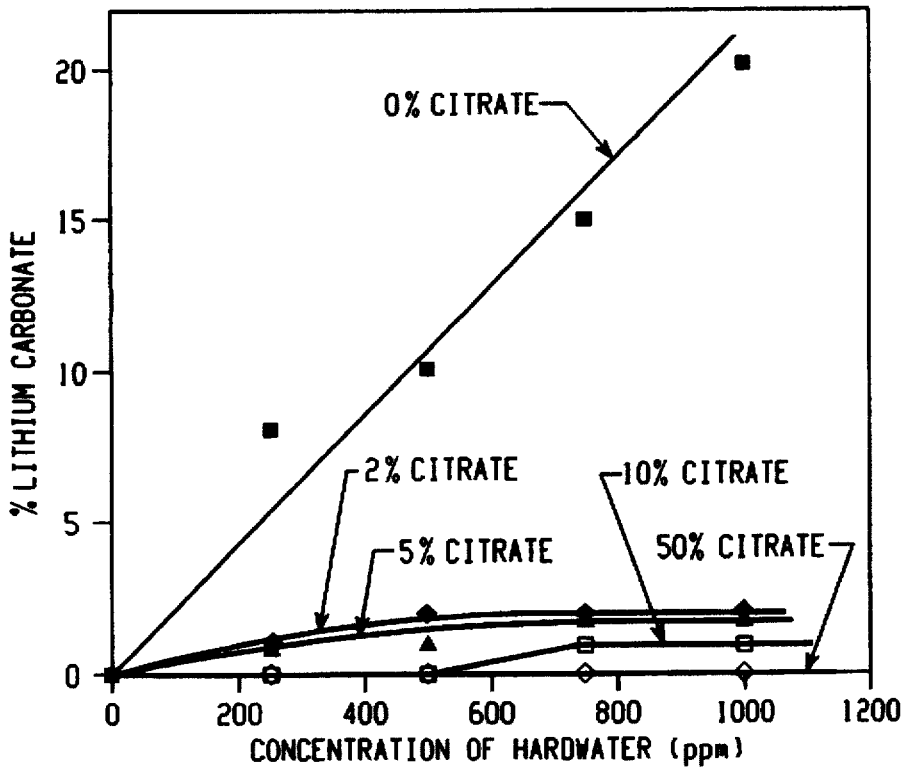

The exact concentration of the chelators is also dependent on the hardness of the water as well as the powdered formulation. The chelators are present in a sufficient concentration to inhibit the formation of lithium carbonate. Residue and hard water buildup are reduced by a high concentration of chelating agents. As shown in FIG. 3, water quality, specifically hardness as measured by calcium carbonate, has minimal effect with an increase in chelating agents. There is a precipitation of lithium carbonate with even small sodium citrate concentrations. In very hard water (about 800 ppm of calcium), there is minimal lithium carbonate formation with more than 10% citrate. In less hard waters (about 500 ppm of carbonate) and soft water, 10% citrate substantially eliminates lithium carbonate formation.

Polyvinyl chloride, stainless steel, aluminum, silicon rubber, polycarbonate, polyethylene, polysulfone rubber, fluorocarbon rubber, acetal, Delrin 500, EPDM rubber, and polystyrene, were each evaluated under continuous exposure to the formulation for an equivalency of 3,000 ten-minute exposures, and evidence complete material compatibility. TABLE 2 illustrates the efficacy of the formulation as a microbial decontaminate. The above-described preferred embodiment of the formulation was mixed in deionized water and very hard water (800 ppm calcium carbonate) to a concentration of 350 ppm of free chlorine and the activity of each solution against *Pseudomonas aeuriginosa* was measured. TABLE 2 shows the results of this testing, where the D-values are in seconds.

TABLE 2

| | WATER QUALITY | |
| --- | --- | --- |
| RUN | DEIONIZED | HARD (800 ppm CaCO₃) |
| 1 | 2.4 | 2.7 |
| 2 | 3.0 | 2.1 |
| 3 | 2.6 | 2.1 |
| AVERAGE | 2.7 | 2.5 |

TABLE 2 shows an acceptable D-value range which correlates to a kill rate of less than five minutes. In the D-value determination:

$D = $ exposure time (in seconds)$/(\log N_i - \log N_f)$ $N_i =$ initial CFU/ml $N_f =$ final CFU/ml.

The above-described formulation is effective as an emulsifier to prevent the clotting of blood accumulation on surfaces. The addition of sodium citrate, sodium gluconate, and other related salts and compounds in conjunction with surfactants tend to act to prevent the accumulation on surfaces by lowering the surface free energy of the material which constitutes the surface.

As shown in TABLE 3, the ability of the formulation to remove dried organic materials from the surface of a glass slide improves with the addition of surfactants. In TABLE 3, a subjective scale is used to evaluate a reduction of protein-rich soil from the surface of a slide during a one (1) minute soak. Each value in TABLE 3 is the average of 5 trials, with a score of 5 indicating no soil removal and a scale of 0 denoting substantially complete soil removal.

TABLE 3

| Sodium Citrate (%) | Pegol (%) | Igepal (%) | Average Score |
| --- | --- | --- | --- |
| 0.0 (control) | 0.0 | 0.0 | 5.0 |
| 2.3 | 0.1 | 0.1 | 2.6 |
| 2.3 | 1.0 | 1.0 | 2.3 |
| 2.3 | 5.0 | 5.0 | 1.9 |

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A dry decontaminant composition which is activated with tap water to form a solution for cleaning and decontaminating blood, fat, protein, and other biological residues from surfaces, the composition comprising:
   (a) lithium hypochlorite,
   (b) a citrate salt in sufficient concentration to inhibit precipitation of insoluble carbonates from the tap water and to act as a cutting agent for fat, protein, and other biological residues, and to act as a chelator for blood,
   (c) a pH buffer,
   (d) a stabilizer,
   (e) a corrosion inhibitor, and
   (f) a surfactant.

2. The decontaminant composition as set forth in claim 1 wherein the solution formed by the addition of water has a hypochlorous ion concentration of between 100 and 5000 ppm and the buffer buffers the solution to a pH between 7.0 and 13.0.

3. The decontaminant composition as set forth in claim 1 wherein the stabilizer is selected from the class including: sulfates, chlorides, and chlorates.

4. The decontaminant composition as set froth in claim 3 wherein the stabilizer is selected from the class including potassium sulfate, lithium chloride, and lithium chlorate.

5. The decontaminant composition as set forth in claim 1 wherein the corrosion inhibitor includes a blend of organic and inorganic corrosion inhibitors.

6. The decontaminant composition as set forth in claim 5 wherein the corrosion inhibitors include a mixture of triazoles and molybdates.

7. A decontaminant composition solution for cleaning and decontaminating blood and other biological residue from surfaces, the solution comprising:
   (a) tap water,
   (b) a hypochlorite, which forms a hypochlorous ion concentration of between 100 and 5000 ppm,
   (c) a chelator,
   (d) a stabilizer,
   (e) a corrosion inhibitor,
   (f) a surfactant, and
   (g) a pH buffer which buffers the pH of the solution to between 6.8 and 8.0.

8. The decontaminant composition solution as set forth in claim 7 wherein the chelator is selected from the class consisting of: citrate salts, gluconate salts, ethylenediaminetetraacetic acid, and mixtures thereof.

9. The decontaminant composition solution as set forth in claim 8 wherein the chelator includes a mixture of the citrate salt, the gluconate salt, ethylenediaminetetraacetic acid.

10. The decontaminant composition solution as set forth in claim 9 wherein the sodium citrate, sodium gluconate, and ethylenediaminetetraacetic acid are present in a ratio of substantially 1:1:2 by weight.

11. The decontaminant composition solution as set forth in claim 8 wherein the hypochlorite includes a lithium hypochlorite and the chelator and hypochlorite are present in a ratio of between 2:3 and 3:2.

12. The decontaminant composition solution as set forth in claim 7 wherein the chelator includes a mixture of sodium citrate and sodium gluconate.

13. A dry decontaminant composition which is activated with water to form a solution for cleaning and decontaminating fat, protein, and other biological residue from surfaces, the composition comprising:
   (a) a hypochlorite,
   (b) ethylenediaminetetraacetic acid,
   (c) a citrate,
   (d) a pH buffer,
   (e) a stabilizer,
   (f) a corrosion inhibitor, and
   (g) 2.0–10% by weight of a non-ionic surfactant.

14. The decontaminant composition as set forth in claim 13 wherein:
   the hypochlorite is lithium hypochlorite,
   the buffer is selected from the class including monosodium phosphate, disodium phosphate, sodium chloride, sodium sulfate, lithium hydroxide, sodium citrate, and mixtures thereof,
   the stabilizer is selected from the class including potassium sulfate, lithium chloride, lithium chlorate, and mixtures thereof.

15. The decontaminant composition as set forth in claim 14 wherein the corrosion inhibitor is selected from the class including triazoles, molybdates, and mixtures thereof.

16. In combination a biological waste fluid handling system and powdered cleaning and decontaminant composition therefor comprising:
   (a) an ampule containing a premeasured dose in powdered form of:
      lithium hypochlorite,
      a citrate salt,
      ethylenediaminetetraacetic acid,
      a pH buffer,
      a stabilizer,
      a corrosion inhibitor, and
      a surfactant;
   (b) a mixing chamber for receiving the premeasured reagent dose;
   (c) a supply of water connected with the mixing chamber for dissolving the premeasured reagent dose to form a cleaning and decontaminant solution;
   (d) a waste fluid collection vessel having an inlet for interconnection with a flexible tube through which biological waste fluids are received;
   (e) a vent interconnected with the waste fluid vessel for connecting an interior of the vessel with at least one of atmosphere and a vacuum source;
   (f) at least one vent valve for selectively closing the vent such that the vessel becomes sealed inhibiting further biological waste fluids from being received;
   (g) a level sensor for sensing a level of biological waste fluids in the vessel;
   (h) a spray nozzle mounted in the waste fluid vessel and connected with the mixing chamber such that the cleaning and decontaminant solution is selectively supplied to the spray nozzle for selectively spraying the interior of the vessel with the cleaning and decontaminant solution; and
   (i) a drain valve for selectively draining the waste fluid from the interior of the vessel.

17. The combination as set forth in claim 16 wherein:
   the buffer is selected from the class including monosodium phosphate, disodium phosphate, sodium chloride, sodium sulfate, lithium hydroxide, sodium citrate, and mixtures thereof; and,
   the stabilizer is selected from the class including potassium sulfate, lithium chloride, lithium chlorate, and mixtures thereof.

18. The combination as set forth in claim 17 wherein the corrosion inhibitor is selected from the class including triazoles, molybdates, and mixtures thereof.

19. The combination as set forth in claim 16 wherein the surfactant is between 2.0% and 10% of the premeasured reagent dose by weight.

20. The combination as set forth in claim 16 further including:
- an automatic control connected with the level sensor, the vent valve, the drain valve, and a valve for controlling flow the decontaminant solution to the spray nozzle, the automatic control responding to the level sensor sensing that the vessel has reached a predetermined level by closing the vent valve until the receipt of biological waste fluid has been terminated, opening the drain valve and vent valve to drain the vessel, opening the decontaminant solution control valve for causing the interior of the vessel to be sprayed with the decontaminant solution, and closing the drain valve before closing the decontaminant solution supply valve such that a volume of the decontaminant solution is retained in the vessel for decontaminating next received biological waste fluid.

21. A dry decontaminant composition which is activated with water to from a solution for cleaning and decontaminating blood and other biological residue from surfaces, the composition comprising:
- 17.5–80.0% by weight lithium hypochlorite;
- 5.0–30.0% by weight citrate salt;
- 0–11.3% by weight ethylenediaminetetraacetic acid;
- 0–30.0% by weight gluconate salt;
- 1.5–6.6% by weight corrosion inhibitors including triazoles, molybdates, and mixtures thereof;
- 2.0–10% non-ionic surfactants;
- a buffer for buffering the solution to a pH of 6.8 to 8.0; and,
- stabilizers.

22. The decontaminate composition as set forth in claim 21 wherein the buffer and the stabilizers include:
- phosphates, and
- lithium salts including lithium chloride, lithium chlorate, lithium hydroxide, and mixtures thereof.

* * * * *